United States Patent [19]

Neigut

[11] Patent Number: 5,378,461
[45] Date of Patent: Jan. 3, 1995

[54] COMPOSITION FOR THE TOPICAL TREATMENT OF SKIN DAMAGE

[76] Inventor: Stanley J. Neigut, 10 Red Rowan La., Plymouth Meeting, Pa. 19462

[21] Appl. No.: 47,236

[22] Filed: Apr. 14, 1993

Related U.S. Application Data

[63] Continuation-in-part of Ser. No. 730,276, Jul. 12, 1991, abandoned.

[51] Int. Cl.$^6$ .............................................. A61K 35/36
[52] U.S. Cl. .................................... 424/94.1; 514/460
[58] Field of Search ........................ 424/94.1; 514/460

[56] References Cited

U.S. PATENT DOCUMENTS

| | | | |
|---|---|---|---|
| 3,658,648 | 4/1972 | Nakao et al. | 435/133 |
| 4,156,718 | 5/1979 | Bliznakov | 424/94.1 |
| 4,617,187 | 10/1986 | Okuyama et al. | 514/689 |
| 4,654,373 | 3/1987 | Bertelli | 514/690 |

OTHER PUBLICATIONS

Harry's Cosmeticology, 6th Ed., Leonard Hill Books, 1973.
E. G. Bliznakov, M.D. and G. R. Hunt, *The Miracle Nutrient Coenzyme $Q_{10}$*, Bantam Books, pp. 140-145, 172-173, 184-187.
L. Kenton, *Ageless Ageing*, pp. 185-193.
R. A. Passwater, "The Antioxidants," *A Good Health Guide*, pp. 4-8, 13.
Tetsuo Ohjuma et al., "Intensification of Host's Immunity by Sqalene in Sarcoma 180 Bearing ICR Mice,": 6 *J. Pharm. Dyn.* 148, 148-151 (1983).
Abstract: "Squalene $C_{30}$, Squalane $C_{30}H_{62}$".
C. A. Auguet, A. M. Casanovas, R. Celades, "A New Source of Squalane,":*DCI*, pp. 51-54 (Nov. 1988).
F. S. Goulart, "Squalane: Healer from the Sea," *The Nutrition and Dietary Consultant* (Jun. 1988).
Abstract: Giovannini, et al., "Skin Penetration of $CoQ_{10}$ in the Rat," 10 *Int. J. Tissue React.* 103 (1988).

Primary Examiner—Marian Knode
Assistant Examiner—Jean C. Witz
Attorney, Agent, or Firm—John W. Logan, Jr.

[57] ABSTRACT

The present invention provides a composition and method for the topical treatment of skin damage, including injury caused by toxins, radiation, and aging. The composition of the present invention employs a combination of a carrier, a ubiquinone, and vitamins A and E to provide a balm of various desired consistencies. The balm of the present invention can be applied directly to a site of skin damage, thus avoiding waste of expensive active ingredients and possible off-site toxicity. The present invention has proven highly effective in treating a wide variety of skin damage, including trauma, discoloration, dryness, loss of elasticity, wrinkles, and periodontal disorders.

7 Claims, No Drawings

COMPOSITION FOR THE TOPICAL TREATMENT OF SKIN DAMAGE

This application is a continuation-in-part of my co-pending application Ser. No. 730,276, filed Jul. 12, 1991 now abandoned.

BACKGROUND OF THE INVENTION

1. Field of the Invention

The present invention relates to compositions and formulations for the treatment of skin disorders or damage in various animals, including humans, and specifically the treatment of hypertrophic and keloid scar tissue, acute phototoxicity, hyperpigmented lesions, skin discoloration, keratosis, and skin hardening. More particularly, the present invention relates to particular formulations of such compositions and method of using the same for the treatment of the above skin disorders and similar problems.

2. Description of the Prior Art

It is known that the process of oxygen based metabolism through the conversion of food to energy forms the foundation of life. While oxidation/reduction (or "redox") reactions are essential to life processes, they also are known to contribute to the process of aging. Oxidation produces potentially toxic and destructive molecules known as free radicals, which are electrochemically unstable species of elements or molecules.

Free radicals have an unbalanced number of electrons when compared with stable counterparts, thus providing them with an electrical charge. As a result, free radicals tend to seek electrical balance by sharing electrons with surrounding stable molecules. This can create chain reactions of free radical production which can lead to serious cellular imbalance.

Even though free radicals are present in all biological systems and they perform necessary functions therein, they are also believed to be responsible for many of the problems with the body at a cellular level. If free radical production proceeds out of control, it can precipitate relentless destruction and degeneration of the body as a whole, including causing inflammation, cellular injury, and protein and cell destruction.

It is also known that a distinct relationship exists between aging and lipid peroxidation caused by the interaction of free radicals on fats and oils at a cellular level. These peroxides tend to join with other lipids and create more peroxides and free radicals. This can lead to serious damage to organelles in the cell, to the cell membrane, and to the ability of DNA and RNA in the cell to replicate. Peroxidation and free radicals are believed to be a primary cause of cell mutation and cancer. By protecting the body and tissues from oxy-stress (i.e. free radical and peroxide damage), it is believed that the rate of aging and susceptibility to disease can be dramatically reduced.

When free radicals react with molecules of protein in cell or tissue, long chain proteins become cross-linked (i.e. molecularly bound together and tangled). Cross-linking is also known to be accelerated by environmental factors, such as exposure to pollutants, heavy metals, and ultra-violet light and other forms of radiation.

Cross-linking of the protein collagen is a phenomenon fundamental to age degeneration. At an internal level, cross-linking of collagen is believed to cause arteriosclerosis and cancer; at a more superficial level, cross-linking can lead to skin wrinkling and sagging. Cross-linking of various proteins, such as collagen, elastin, and reticulin, also can lead to diminished ability of the cell to absorb and metabolize nutrients and to dispose of waste.

While a body is young, it produces special enzymes which are necessary for proper metabolism and which are effective at breaking down and preventing excessive cell cross-linking. One such group of enzymes are ubiquinones which contribute to a variety of cell functions, including the manufacture of adenosine triphosphate (ATP), as well as assisting in oxygen transfer, and acting as a antioxidant to protect cells from free radicals. Ubiquinones include vitamin $K_1$, which serves as a antihemorrhagic agent, and the Q coenzymes, such as Co-$Q_4$ through $Q_{15}$. Coenzyme $Q_{10}$ is produced in the liver and, as is discussed below, has been linked to a variety of beneficial results when taken internally.

As the body ages, accumulation of free radicals accelerates at the same time that the production of protective enzymes diminish. It is believed that the combined effect of these two factors contribute greatly to the process of aging. By way of example, Coenzyme $Q_{10}$ has been identified as an important enzyme necessary in metabolism, a powerful antioxidant, and an immunostimulating agent. It is known that the body loses its ability to synthesize this molecule as it ages, leaving diet as the only source for it.

One study has shown that laboratory animals which were administered coenzyme $Q_{10}$ internally had a 56% increase in longevity as compared with a control group. The coenzyme group also had more youthful appearance until the end of their lives.

Not surprisingly, considerable interest has been generated in studying the ubiquinones, and particularly coenzyme Q. U.S. Pat. No. 3,658,648, issued Apr. 25, 1972 to Nakao et al., discloses a process for the production of coenzyme Q. U.S. Pat. No. 4,156,718, issued May 29, 1979 to Bliznakov, discloses that internally administering coenzyme $Q_4$ to $Q_{13}$ to animals can be effective in controlling and reversing immunological senescence.

One of the major problems with coenzyme Q is that it is found in extremely low quantities in nature and has been relatively difficult to extract or chemically synthesize. Accordingly, it is expensive and of limited availability. As a result, a program of treatment employing coenzyme Q is necessarily constrained due to the expense of the coenzyme. For many common minor aging problems, such as loss of suppleness and elasticity of the skin (i.e. resulting in dryness, wrinkling and similar cosmetic problems), oral doses of coenzyme Q are not economically practical. Additionally, the quantity of oral doses of coenzyme are also constrained in that there is no way to target the coenzyme for a particular injury site; thus, total intake must be limited to avoid possible toxicity in the body as a whole.

Despite the successes with the internal administration of coenzyme Q in controlling and reversing the process of aging in animals, prior to the present invention applicant was unaware of any instance where coenzyme Q was suggested to be used topically to address skin injury, aging or other damage. In fact, upon information and belief, even in treating periodontal diseases, treatment with coenzyme Q has been administered in oral doses transported through the blood system. Furthermore, there is a lack of teaching or suggestion in the literature concerning a method or formulation for providing optimal ubiquinone uptake by the skin.

Subsequent to the present invention, applicant has become aware of one instance where skin penetration of coenzyme $Q_{10}$ was investigated in rats. Giovannini, L. et al., "Skin Penetration of $CoQ_{10}$ in the Rat," 10 *Int. J. Tissue React.* 103-05 (1988). This study indicated that the coenzyme is absorbed by the skin of the rat at a rate proportional to its concentration when suspended in olive oil. However, the authors apparently did not investigate whether pharmacological treatment was possible or practical. Moreover, the authors provide no suggestion of particular formulations which may provide successful topical therapeutic treatment.

Although other substances have been employed to treat skin damage problems, none have proven fully satisfactory. Various vitamins, such as vitamin E, have been applied to skin alone and in conjunction with other preparations, but these have met with limited therapeutic success. Similarly, various preparations employing squalane and squalene have been applied to the skin, but these have also proven less than completely therapeutically acceptable.

Accordingly, it is a primary object of the present invention to provide a formulation and method for effectively treating skin damage in humans and other animals, including damage due to injury and aging.

It is a further object of the present invention to provide such a formulation and method which permits topical application of active chemical constituents directly to an injury site, allowing maximum doses with minimum risk of toxicity to other cells.

It is another object of the present invention to provide such a formulation and method which permits topical application to an injury site in order to avoid non-site waste of expensive chemical constituents, thus limiting the cost of treatment and making such treatment more widely available.

It is yet another object of the present invention to provide a formulation and method for the topical application of coenzyme Q to injury sites on skin.

It is an additional object of the present invention to provide a formulation and method for the topical application of coenzyme Q to injury sites on skin which maximizes the uptake and effectiveness of the coenzyme.

A still further object of the present invention is to provide a formulation and method for the topical application for the treatment of hypertrophic and keloid scar tissue, acute phototoxicity, hyperpigmented lesions, skin discoloration, keratosis, and skin hardening.

These and other objects of the present invention will become evident through review of the following specification.

SUMMARY OF THE INVENTION

The present invention provides a composition for topical treatment of skin damage. The invention provides a mixture of an oil-based carrier, such as squalane, a coenzyme $Q_4$ to $Q_{15}$, and vitamins A and E. The mixture forms a balm of any desired constituency which can be applied directly to the site of skin damage, with extremely low risk of off-site toxicity and very little waste. The combined composition has proven to be remarkably effective in penetrating the skin and treating many forms of skin damage, such as hypertrophic and keloid scar tissue, acute phototoxicity, hyperpigmented lesions, skin discoloration, keratosis, and skin hardening. The present invention is particularly effective in combating skin damage associated with aging.

In the preferred embodiment, the present invention provides a composition of squalane, coenzyme $Q_{10}$, vitamin A, and vitamin E. The composition may comprise any form of balm, including but not limited to a liquid, emulsion, cream, ointment, suspension, powder, bath oil, emollient or powder. Additionally, vitamin D, gamma linolenic acid, and/or cis linoleic acid may be added to the composition of the present invention to further improve its therapeutic effect.

The present invention has proven to be vastly more effective than existing methods of topical treatment. Moreover, the present invention provides means for direct application of ubiquinones to an injury site, dramatically increasing the effectiveness of treatment at minimal expense and minimal risk of off-site toxicity or waste.

DETAILED DESCRIPTION OF THE INVENTION

The present invention provides a composition for the topical treatment of skin damage in humans and other animals and method of producing and using such composition. The present invention is effective at treating many forms of skin damage, including damage due to injury, trauma, and exposure to toxins and radiation, and particularly damage associated with aging.

The composition of the present invention comprises a unique mixture of four major ingredients: an oil-based carrier; a ubiquinone; vitamin E; and vitamin A. As is discussed below, the ubiquinone is preferably a coenzyme Q of the formula:

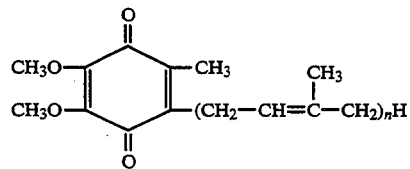

in which n is 4 to at least 15. In coenzyme $Q_{10}$, employed in the preferred embodiment of the present invention, n is equal to 10. One method of production of coenzyme Q is disclosed in U.S. Pat. No. 3,658,648. One commercial source for coenzyme $Q_{10}$ is Twin Laboratories, Inc. of Ronkonkoma, N.Y. Twin Laboratories sells a composition of coenzyme $Q_{10}$ for internal consumption under the tradename MAXILIFE $CoQ_{10}$. This formulation contains 10 mg of coenzyme $Q_{10}$, as well as vitamins E, C, various Bs, and selenium, zinc and other antioxidants.

As is noted in U.S. Pat. No. 4,156,718, the activity of coenzyme Q is believed to be animal specific, and different coenzyme Q predominate in different animals. For most animals, coenzymes lower than $Q_4$ show little activity. For humans, coenzyme $Q_{10}$ has shown the greatest activity, although coenzymes with a composition of $Q_{11}$ to $Q_{15}$ are also believed effective. Although not readily available for testing, it is believed that a formula above $Q_{15}$ may also provide the benefits of the present invention.

A balm of the present invention is created by heating the carrier to between 120° and 150° F., with approximately 140° to 150° F. preferred, to improve the solubility of the coenzyme therein. Once heated, the carrier is divided into two portions of a ratio of approximately 10:90 to 20:80. The coenzyme is then dissolved into the smaller of these portions. This concentrated solution should then be thoroughly dissolved in the remaining heated carrier, making sure that there is no residual particulate matter. The solution is then cooled to at least 90°–95° F.

To the above solution vitamins A and E are added and the solution is completely mixed to make sure that there is a complete distribution and dispersion of all ingredients. Additionally, vitamin D, as well as gamma linolenic acid, and cis linoleic acid may be added to this solution. It is believed that the vitamins A and E act synergistically with the coenzyme and help to potentiate its effect in the skin cells. The addition of vitamin D, gamma linolenic acid and/or cis linoleic acid have been observed as improving this effect. The order of addition of these ingredients into the solution should be as follows: vitamins A, D, E, gamma linolenic acid, and cis linoleic acid.

The finished product must be free of bubbles and all residue. Filtration through a 450–1500 nanometer pore size filter, depending upon pressure used, may be required if any particulate remains out of solution when it is brought to room temperature.

The following table represents the preferred ranges of components of the preferred embodiment of the present invention for each 100 ml of squalane carrier:

| Component | Minimum (if present) | Maximum | Optimum |
|---|---|---|---|
| Squalane ($C_{30}H_{62}$)/ squalene ($C_{30}H_{50}$) | 100 ml (40% by wt.) | 100 ml | 100 ml (60% by wt.) |
| Vitamin A | 50,000 iu | 750,000 iu | 500,000 iu |
| *Vitamin D | 1,000 iu | 12,000 iu | 8,000 iu |
| Vitamin E | 1,200 iu | 18,000 iu | 12,000 iu |
| Coenzyme $Q_{10}$ | 250 mg | 3,000 mg | 1,000 mg |
| *Gamma Linolenic Acid | 0 | 2,000 mg | 600 mg |
| *Cis Linoleic Acid | 0 | 16,000 mg | 4,000 mg |
| *Lecithin | 0 | 9,600 mg | 4,800 mg |
| *L. Cysteine | 100 mg | 2,000 mg | 500 mg |
| *L. Methionine | 100 mg | 2,000 mg | 500 mg |
| *Sodium Selenite | 500 mcg | 2,000 mg | 50 mg |
| *Dimethyl Glycine | 1,000 mg | 9,000 mg | 2,500 mg |
| *Super Oxide Dismutase | 1,000 iu | 8,000 iu | 4,000 iu |
| *Zinc Oxide (Gluconate) | 50 mg | 1,000 mg | 400 mg |

* = Desirable but not essential

The optimum formula has been determined empirically by observation of the effects on the skin of twenty-five people for a period of eight months and from their responses. The minimum formula is based upon the smallest amount of components which provided any observable benefit.

The maximum formula is based more upon economic rather than technical or therapeutic considerations and on the potential toxicity of vitamins A and D at higher concentrations, used over large areas, and/or for long periods of time. A study of Co-$Q_{10}$ conducted in animals suggests that the benefits derived may be proportional to the level of concentration of the coenzyme and the period of time it is available for administration. Considerably higher concentrations of coenzyme may be justified in a suitable carrier, such as squalane, for certain kinds of skin disorders, provided that cost is not an important factor.

Squalane, including squalene, has been shown to be a very effective transport medium for the other ingredients. However, it has been found that other carriers can be used with similar effectiveness. Accordingly, the carrier may comprise any non-toxic organic or inorganic carrier or transport medium, such as but not limited to, plant-derived oils, animal derived oil, aqueous solutions, mineral oils, dimethyl sulfoxide (DMSO), glycerin, propylene glycol, and similar solutions. Vitamin D, gamma linolenic acid and cis linoleic acid have all proven to enhance the activity of the composition of the present invention, but none are deemed essential to the functioning of the present invention.

The present invention provides a balm which may be applied directly to an injury site. Depending upon the application, the balm may take the form of an oil or other liquid preparation, a cream, a paraffin-based or similar preparation, a dried powder, a salve, or any other suitable application. Due to the nature of the active ingredients, and to maximize the speed of uptake by the skin, a liquid form is preferred.

In application, the patient's skin is first thoroughly cleaned around the site of damage. The balm is then applied liberally to the site and is allowed to soak in. For an oil or liquid balm of the formulation discussed above, the balm should be left on the site for at least 1 to 3 minutes. In some instances, it may also be beneficial to apply the balm to the site and then wrap the site with bandages or other occlusive material to assure that the balm will remain in contact with the site as long as possible. For instances where bandaging is not practical, it may be preferred to suspend the active ingredients in a cream or similar preparation which will be retained at the site of damage for a longer period of time.

Without intending to limit the scope or application of the present invention, applicant believes that the present invention functions under the following principles. The two primary ingredients, squalane/squalene and the coenzyme, are biogenic. Squalene is synthesized in the sebaceous glands of the body and coenzyme $Q_{10}$ is synthesized in the liver.

In humans, squalane comprises up to 10% of the sebum. It is a natural emollient which is miscible with the interfibrillar glycoproteins, improves skin respiration, has a high rate of skin penetration, and reduces moisture loss. Even though the sebaceous glands increase in size as aging takes place, squalane synthesis is reduced considerably as a result of aging. Squalane production is also adversely affected by exposure to radiation, chemicals, and other environmental factors.

As has been noted, coenzyme Q has been shown to play a key role in the human immune system, and to provide beneficial results when taken by injection or oral administration. Coenzyme Q, and particularly $Q_{10}$, also has been used extensively as a prophylaxis for supporting immunological response against attacks to the immune system and for treatment of heart and other vascular problems. It has also been employed internally in the treatment of periodontal disease.

The present formulation is believed to work effectively as a skin nutrient because it reduces loss of bound water in skin tissue. It is believed to retard cross-linking within tissue cells by reducing lipid peroxidation in the cell's microsomes and mitochondria. Further, the combined presence of coenzyme Q, squalane, and vitamins A and D are believed to help in cell respiration, energy transfer, cell metabolism, and cell waste removal. All this combines to assist in restoring cellular energy without promoting cell proliferation.

Coenzyme Q's ability to add or subtract singlet oxygen from the cell's mitochondria enables it to act as an antioxidant, thereby reducing free radical formation. Vitamin E is known to serve as an antioxidant—reducing or eliminating lipid peroxidation in the cell's microsomes and mitochondria. It is believed that vitamin E and coenzyme Q work together synergistically in respiration and encourage more efficient use of oxygen.

The formula of the present invention has also been shown to be effective in the depigmentation of certain skin discolorations, restoring more normal color, and reduction of skin inflammation attributed to phototoxicity. Although further study is required, it is believed that the present invention may be effective in the treatment of burns, scar tissue, solar keratosis, psoriasis, warts, basal cell carcinoma, and possibly melanoma. Additionally, the present invention may be effectively utilized for topical treatment of periodontal diseases.

The following are examples of formulations of the present invention:

EXAMPLE 1

A mixture of the following components was prepared:

| Squalane ($C_{30}H_{62}$) | 100 ml |
| Vitamin A | 500,000 international unit (iu) |
| Vitamin D | 8,000 iu |
| Vitamin E | 12,000 iu |
| $CoQ_{10}$ | 1,000 mg |
| Gamma Linoleic Acid | 600 mg |

The squalane was heated to 140° F. and divided into two portions of 80 ml and 20 ml. The coenzyme was mixed into the 20 ml of squalane until thoroughly dissolved and the remaining 80 ml of squalane was then mixed into the composition. The composition was cooled to 90° F. and vitamins A, D, E, and gamma linoleic acid were then mixed into the composition in that order. The final composition was filtered through a 1500 nanometer pore size filter to assure that it was free of all bubbles and residue. The final composition is a balm in the form of a transparent oil.

In application for discoloration, wrinkles and dryness, the patient's skin was thoroughly cleaned in the area of treatment and the balm of the above formulation was applied to areas of skin damage. The balm was applied as a drop of oil which was gently rubbed into the treatment area. This treatment was repeated twice daily for approximately 30 to 45 days until improvement occurred. Marked improvement was demonstrated in 15 to 25 days in many cases.

EXAMPLE 2

A mixture of the following components was prepared:

| Squalane ($C_{30}H_{62}$) | 100 ml |
| Vitamin A | 500,000 international unit (iu) |
| Vitamin D | 8,000 iu |
| Vitamin E | 12,000 iu |
| $CoQ_{10}$ | 600 mg |
| Gamma Linoleic Acid | 2,400 mg |
| Ascorbyl Palmitate | 1,000 mg |

This composition was mixed in a manner similar to that outlined in Example 1. Here ascorbyl palmitate was added to squalane heated to 180° F. and thoroughly dissolved. This mixture was then cooled to 140° F. at which $CoQ_{10}$ is added. The solution was cooled to approximately 90° F. and the remaining ingredients were added in the same sequence as outlined in Example 1. In application, this mixture was applied in the manner outlined in Example 1 with equally effective results.

The above variation of the present invention is particularly effective in use for treatment of gum disorders and other periodontal problems by applying the formula to gingiva, mucous membranes, and other areas of the mouth.

EXAMPLE 3

| | Formulae Examples |
|---|---|
| Squalane ($C_{30}H_{62}$) | 100 ml |
| Vitamin A | 700,000 iu |
| Vitamin D | 10,000 iu |
| Vitamin E | 16,000 iu |
| $CoQ_{10}$ | 2,000 mg |
| Gamma Linoleic Acid | 800 mg |
| Lecithin | 4,800 mg |

Squalane is heated to 140° F. to which CoQ10 and Lecithin are added. Mixture is cooled to 90° F. and remaining ingredients are added in same sequence as in example 1.

This example has a higher concentration of $CoQ_{10}$, vitamins A and E and a slightly greater viscosity due to the lecithin. Lecithin is known to have anti-oxidant properties, and because of this characteristic as well as its contribution to viscosity, lecithin provides synergy with the other ingredients.

The above formulation is beneficial when slightly longer skin surface contact and slower penetration is preferred as in such conditions as psoriasis, acne, skin allergies, etc. This formula is excellent for bed time application to damaged/aged skin and to undesirable pigmented areas. Apply as in example 1.

EXAMPLE 4

Formula as in example 1 except Vitamin A is reduced to 250,000 iu and 150 mg of Beta Carotene is added. This same change can be made in example 3 however in this case Vitamin A will be reduced to 350,000 iu and 200 mg of Beta Carotene added.

Beta Carotene is a precursor of Vitamin A but has proven anti-oxidant properties of its own which have not been used for skin application. The application of this formula imparts a slightly orange color to the skin which is easily removed with soap and water. The formulation of example 4 should be used for affected areas not generally visible to the public or when going to bed or as a foundation for make up in visible areas.

EXAMPLE 5

| Squalane ($C_{30}H_{62}$) | 50 ml |
| Propylene Glycol | 50 ml |
| Vitamin A | 500,000 iu |
| Vitamin D | 8,000 iu |
| Vitamin E | 12,000 iu |
| $CoQ_{10}$ | 2,000 mg |
| Gamma Linoleic Acid | 600 mg |
| Lecithin | 2,400 mg |
| L. Cysteine | 500 mg |
| L. Methionine | 500 mg |
| Sodium Selenite | 50 mg |
| Super Oxide Dismutase | 4,000 iu |
| Dimethyl Glycine | 2,500 mg |
| Zinc Gluconate (Zinc Oxide) | 250 mg |
| Corn Starch | 35 g to 125 g - depending upon viscosity desired |

L. Cysteine and L. Methionine are sulphur based amino acids considered to have strong anti-carcinogenic, anti-oxidant properties. Selenium, SOD, zinc and DMG are also considered to be effective anti-oxidants. Zinc also has skin healing properties. It is believed by many researchers and scientists that the factors which contribute to the development of cancer also contribute directly to the aging process. While considerable research has been conducted on the oral administration of anti-carcinogens and anti-oxidants little has been studied regarding topical administration of these compounds for the treatment of skin damage, aging and various skin disorders.

Corn starch has been used as an effective binder to all ingredients. It does not impede skin penetration and gives a smooth velvety feel to the skin. However because of the separation of oil and water soluble ingredients when left standing for a period, an appropriate surfactant emulsifier will have to be utilized to maintain uniformity. Colloidal oatmeal, potato, taro, rice, and other such starches may be substituted for, or used in combination with corn starch.

Squalane is heated to 140° F. to which lecithin and CoQ$_{10}$ are added and completely dissolved. This mixture is then cooled to approximately 90° F. to which Vitamins A, D, E and Gamma Linoleic Acid are added and thoroughly mixed.

Propylene glycol is heated to 140° F. to which is added one at a time the L. Cysteine, L. Methionine, Sodium Selinite, SOD, Zinc and DMG. Ingredients should be completely dissolved and filtered as in example 1.

The propylene glycol mixture, and the Squalane mixture, both of which have been allowed to cool to 90° F. or lower are then thoroughly mixed together by high speed bending to insure uniformity of ingredient distribution.

The above mixture is then blended with corn starch in an amount to achieve desired viscosity. An effective surfactant is added at the appropriate time in the manufacturing process to prevent ingredient separation and maintain long term uniformity.

The above preparation may be manufactured as a low viscosity emulsion or as a viscous ointment depending upon surfactant and/or the amount of starch incorporated into the formula.

A light emulsion is more useful for frequent daily application to exposed damaged skin areas, whereas higher viscosity emulsions or ointments/creams are more beneficial for longer protected skin contact, particularly in the treatment of thick psoriatic plaques which are almost impenetrable to most medication. A viscous emulsion containing 65 g of corn starch has been tested with beneficial results to large thick psoriatic plaque areas, i.e. in the descaling of these areas and in the reduction of local inflammation.

The major inhibiting problem of using the above preparation is the slight disagreeable order of sulphur compounds which tends to intensify with body heat. This can probably be masked or mitigated by the addition of an acceptable fragrance.

EXAMPLE 6

Formula as in example 5 except propylene glycol is reduced to 25 ml and 25 ml glycerin is added. Manufacturing is the same except that water soluble materials are dissolved in heated propylene glycol to which is then added glycerin at 140° F. These are mixed and blended together before being added to the squalane mixture.

Glycerin has been used as a skin lubricant and moisturizer for many years. This ingredient improves the preparations viscosity and adherence quality to the skin and imparts a slight elasticity. Almond oil or black current oil may be substituted for glycerin which also helps to improve odor. However, the almond or black current oil must be added to squalane mixture before blending with propylene glycol mixture.

A number of limited case studies have been performed for specific skin disorders. These case studies have been compared with the treatment on the same patient of other suggested products. In each instance the results were exceptional.

In these case studies, patients were treated with the inventor's formula patterned after Example 1 above. This formulation was as follows:

|  | % by Weight |
|---|---|
| Squalane | 63 |
| Vitamin A | 8 |
| Vitamin D | 5 |
| Vitamin E | 16 |
| CoQ$_{10}$ | 1 |
| Gamma Linoleic Acid | 3 |
| Lecithin | 4 |

A formulation, referred to below as Formula A, containing ubidicarenone (CoQ$_{10}$) and squalane was used as a control test. Formula A was as follows:

|  | % by Weight |
|---|---|
| Stearyl Alcohol | 5 |
| Stearic Acid | 2 |
| Hydrogenated Lanolin | 2 |
| Squalane | 6 |
| Isopropyl Myristate | 4 |
| Polyoxethylene (25 moles) cetyl alcohol ether | 3 |
| Glycerin Monostearate | 2 |
| Ubidecarenone | 0.3 |
| Propylene Glycol | 5 |
| Butyl Paraben | 0.2 |
| Purified Water | 70.5 |

This is Example 1 of U.S. Pat. No. 4,617,187 to Okuyama et al.

A third formulation, referred to below as the Vitamin Formula, or Formula B, containing Vitamins A, D and E in an olive oil base, was also used as a control test. This formulation is as follows:

|  | % by Weight |
|---|---|
| Olive oil | 67 |
| Vitamin A | 8 |
| Vitamin D | 6 |
| Vitamin E | 19 |

Some of the case studies are as follows:

Case Study I

A 53 year-old female with lentigo senilis, commonly known as "age or liver" spots on her face, arms, and back of hands. The severely affected areas were mottled, unevenly pigmented, and slightly indurated.

Six similarly affected areas were selected comprising two on the face, two on the upper arms, and two on the back of the hands. The areas were cleaned, rinsed, and dried prior to application, and the woman was instructed to apply each of the above test formula to designated areas three times per day. The woman was observed once each week and examination made of each of the test sites.

At the end of the first week the areas treated with the inventor's formula showed signs of lightening and less induration, neither of which were observed at the areas treated with Formula A or Formula B. By the end of the sixth week of application of the inventor's formula, the lighter pigmented areas were virtually restored to normal color and texture and the hyperpigmented darker areas had become significantly lighter. Induration was non-existent. The areas treated with Formula A for the same period did not exhibit any significant difference, particularly with regard to the hyperpigmented areas, and little change was noted with regard to lessening induration. No changes in pigmentation were observed at areas treated with the Vitamin Formula (Formula B), and induration was only slightly improved compared to Formula A.

Case Study II

A male 65 years old with keloids and hypertrophic scar tissue on the right arm, right shoulder and right leg, all having resulted from an automobile accident during 1987 with traumatic injury and subsequent clean-up surgery to those areas. These areas had been previously treated by post-operative intralesional injections of steroids, but without significant improvement. At the time the patient was first seen, there appeared to be some reddened inflamed areas at the scar sites, but these were believed to have been caused by surface abrasion. Keloids and hypertrophic scars are characterized by excessive collagen formation. Since these formations have certain similarities to collagen metabolism, cross-linking, and skin aging, it was believed and claimed in the inventor's patent application that the application of his formula to this skin disorder could prove to be beneficial.

Three areas were selected, i.e., one at the inner elbow comprising a hypertrophic scar approximately 12 cm long, the second a similar scar approximately 9 cm in length located on the upper arm near the bicep muscle, and a third hypertrophic scar on the shoulder approximately 7 cm in length. All three areas exhibited several keloid formations.

Because of the therapeutic difficulties inherent in the treatment of keloid and hypertrophic scar tissue, it was decided to use an occlusive dressing for each of the three formulae to maintain longer skin contact and improve the opportunity for more rapid skin penetration. The areas were cleansed, rinsed, and dried and one of each of the three formulae being tested was applied to a specifically designated site twice per day and sealed with a plastic overwrap. The first application was in the morning and remained for a period of approximately 8 hours, and the second application at night which remained in place for a period of approximately 10 hours.

At the end of 14 days marked differences were observed between the three sites. The scar treated by the inventor's formula had decreased its linear dimension approximately 15% and was flatter. No inflammation had been observed. Of the three keloids located in the area treated by my formula, all had reduced approximately 10% in size. Observation of the sites treated by Formula A and the Vitamin Formula (Formula B) did not exhibit any significant improvement on hypertrophic scar or keloid tissue as compared to the area treated by the inventor's formula, but inflammation had shown improvement.

On the thirty-fifth day after beginning the test, the three sites were again compared. There had been a 30% reduction in the linear dimension of the scar treated by this formula and the scar had almost completely flattened out. The keloids and the scar had almost completely flattened out. The keloids treated in that area had been reduced approximately 50%.

The area treated by Formula A showed only negligible positive changes with regard to hypertrophic scar and keloid tissue. The area treated with the Vitamin Formula (Formula B) showed no discernible positive changes with regard to the above. Occlusive dressing had to be discontinued at this time, however, because the site treated by Formula A began to show signs of irritation. This might be attributed to the subject's sensitivity to one or more of the ingredients in that formula.

Case Study III

A 47 year-old female with Xeroderma Pigmentosum. The outward manifestations of this condition are brown discoloration, cracking and ulceration of the skin. Although this condition may have more serious underlying systemic considerations and consequences, the writer was limited to test treatment only of the cosmetic effects. Areas selected for treatment were the shoulder, lower back, and thigh. Because the lower back is not as accessible to the patient, her husband was instructed in the test program and taught to apply the specific formula designated for that area.

Usually in difficult to treat skin conditions, the extremities and lower back are usually the most recalcitrant to most forms of therapy. Consequently the lower back was selected as the site for the inventor's formula, the thigh for Formula A, and the shoulder for the Vitamin Formula (Formula B).

Occlusive dressings using the same protocol as in Case Study II had been applied for the first 14 days. The subject was seen every 7 days to make sure there were no problems developing. The dressings were removed and sites compared on the fourteenth day.

The site to which the inventor's formula had been applied indicated a definite reduction in brown discoloration, less cracking and the formation of granulation tissue in ulcerated areas. There was significantly less keratosis, and considerably less discomfort in that area which was conveyed by the subject. The site treated with Formula A did not exhibit any significant change in discoloration. Although granulation tissue in ulcerated areas was perceived, it was approximately 50% less than that exhibited on the site of the inventor's formula. A reduction in keratosis was not observed. The site to which the Vitamin Formula (Formula B) had been applied, although generally less recalcitrant to treatment, showed no change in discoloration, very little formation of granulation tissue, but a slight improvement in keratosis. By the forty-second day of treatment the site treated by the inventor's formula was demonstrably free of discoloration. Fissures and ulcerated areas had healed and appeared to be normal in color, texture, tone and thickness.

The site treated with Formula A still had marked signs of brown discoloration. Some fissures remained. Ulcerated areas had improved but the color had been mottled and the scar tissue was not as flat. Keratosis was still evident but somewhat improved. The site treated by the Vitamin Formula (Formula B) did not exhibit any significant positive change in the condition. Improvement in keratosis was approximately to the same degree as with the Formula A test site.

Case Study IV

A 65 year-old male with recalcitrant psoriasis covering approximately 70% of his body.

This subject's condition was sufficiently severe to justify inpatient treatment in a renowned hospital under the control of the Department of Dermatology.

The patient's therapy regimen was the Goekerman treatment which comprises the alternate topical application of coal tar, coal tar baths, occlusive topical application of steroids, and daily increasing exposure of affected areas to UVB. Within a two-week period the patient showed substantial improvement but there still remained a few resistant large plaque areas on the lower back, knees and thighs of the patient. The patient was discharged from the hospital, but out-patient UVB exposure was recommended to be continued three times per week for a minimum of 6 to 8 weeks as well as the continued application of steroids.

By the end of four weeks of out-patient UVB and steroid treatment, the remaining plaque areas were less keratotic but still somewhat indurated. The plaques and surrounding tissue, however, were very mottled in color and uneven in texture. Areas treated with topical steroids tended to be less pigmented than normal tissue even though both areas had been subjected to the same degree and intensity of UVB. The normal surrounding tissue was unevenly colored and contained a number of hyperpigmented lesions.

At this time the patient agreed to test the three formulae on three sites, each of which contained psoriatic and normal tissue. The subject agreed to discontinue topical application of steroids to those sites for the duration of the test period. The subject, however, continued with the UVB treatment.

The subject was instructed to apply Formula A to the left thigh and knee, the inventor's formula to the right thigh and knee, and the Vitamin Formula (Formula B) to the right shin and forearm. No topical steroids were to be used at these sites. The remaining areas of the body were to be treated in the same manner as previously instructed by the dermatologist. Each of the test sites were similar in the thickness of the plaques and in the general texture and degree of hyperpigmentation, although the distribution varied with each site. This variation was not sufficient to influence comparative results. Formulae were applied twice daily, one in the morning and one at bedtime with an occlusive dressing. Subject was instructed not to apply any of the formulae prior to UVB exposure.

Two weeks after initiation of the test, the sites were examined and significant differences were observed. The site to which the inventor's formula had been applied was less mottled, more elastic and all of the hyperpigmented spots had been lighter in color, as compared to the Formula A and Formula B sites. The test site for the inventor's formula was also much more evenly colored, softer and more elastic than the untested sites which were conventionally treated.

After four weeks of treating the site used for the inventor's formula, the plaque areas had completely flatted out. The plaque areas had been restored to a normal healthy color, and no discernable difference of plaque texture, color or elasticity could be observed as compared to healthy surrounding tissue. It was quite unexpected to discover that the hypopigmented plaques had become darker while the surrounding hyperpigmented areas had become lighter, thus providing a more even color. The lighter pigmented lesions had completely disappeared and the very dark pigmented lesions had become significantly lighter, more dispersed, and much less noticeable.

The Formula A sites, although they exhibited improvement, were not evenly colored, and the hyperpigmented lesions in tissue surrounding the plaques were not significantly lighter. The plaques were not as flat, nor had there been any real dramatic depigmentized areas. There was some evidence of plaque thickness and residual induration, none of which were observed at the inventor's sites.

At the sites using the Vitamin Formula (Formula B) no significant improvements with regard to lightening of hyperpigmented lesions or repigmentation of depigmented plaques were observed. At these sites, both plaque and surrounding tissue still showed evidence of mottling. Plaques were not as flat, soft or elastic as compared to the inventor's sites, but there was somewhat less induration compared to the Formula A sites.

In conclusion, based upon the above described tests, the results clearly indicate that the inventor's formula provides improved significant and unexpected positive effects, which are not demonstrated by either Formula A or the Vitamin Formula (Formula B).

Case Study V

A female patient, age 60, was suffering from acute phototoxicity, a condition considered by most dermatologists to be irreversible. The skin was a purplish-red color with visible swelling and inflammation of surface capillaries. The patient's face was used as the test site.

On one side of the patient's face a solution was applied containing 0.75% $CoQ_{10}$ suspended in olive oil. On the other side of the patient's face a formulation made in accordance with Example 1 of the present application was applied, including the following components:

|  | % by Wt. |
| --- | --- |
| Squalane ($C_{30}H_{62}$) | 66.4 |
| Vitamin A | 8.3 |
| Vitamin D | 5.5 |
| Vitamin E | 17.7 |
| $CoQ_{10}$ | 0.75 |

It should be noted that this formulation differs from Example 1 of the present application only in that it contains less than the 1.2% of $CoQ_{10}$ identified therein.

The same amounts of each respective formulae were applied to each of the test sites. Applications were made two times daily.

It was observed initially that the formula of the present invention penetrated the skin quickly and more completely than the $CoQ_{10}$ suspension in olive oil formula, with much less residual surface oil on the site. The patient was asked to wait at least two minutes to permit skin penetration before washing.

After one week, the side of the face treated with the formula of the present invention exhibited a significantly lower degree of inflammation and reduced visibility of swollen capillaries as compared to the $CoQ_{10}$ suspension in olive oil treated side. After fourteen days the side treated by the formula of the present invention had a more normal skin color, smoother texture and virtually no visible capillary inflammation as compared to the $CoQ_{10}$ suspension in olive oil treated side.

Case Study VI

A more substantial difference between the two formulae was observed in the treatment of pigmented (aging/liver) spots, and raised pigmented lesions ranging in thickness from 0.5 mm to 1.25 mm. In the case study two patients were used, one female age 70 and one male age 74.

From prior experience it was known that a higher concentration of $CoQ_{10}$ would be required if rapid results were to be expected. Therefore, a 1.5% solution of $CoQ_{10}$ was used in both formulae, i.e. 1.5% $CoQ_{10}$ dissolved in olive oil for one treatment, and a 1.5% $CoQ_{10}$ concentration incorporated in the formula of Example 3 of the present application, including:

|  | % by Wt. |  |
|---|---|---|
| Squalane ($C_{30}H_{62}$) | 63.1 |  |
| Vitamin A | 7.9 |  |
| Vitamin D | 5.3 |  |
| Vitamin E | 16.8 |  |
| $CoQ_{10}$ | 1.5 | (versus 1.1% per disclosure) |

Each formula was applied to designated dark pigmented lesion sites three times per day. These lesions were located on the arms, shoulders, and forehead of one patient, and on the temple, forearm, and wrist of the other patient. The backs of one hand of each patient which contained flat pigmented areas, sometimes referred to as "age" or "liver" spots, were also treated with the respective formulae.

Within two weeks the raised pigmented lesions which were treated with the formula of the present invention were considerably lighter, and in a few instances had completely disappeared as compared to the similar areas treated with the $CoQ_{10}$ suspension in olive oil.

Although particular embodiments of the present invention are disclosed herein, it is not intended to limit the invention to such a disclosure and changes and modifications may be incorporated and embodied within the scope of the following claims.

What is claimed is:

1. A balm for the topical treatment of skin damage comprising a mixture of:
   a carrier solution chosen from the group consisting of squalene and squalane, said carrier solution comprising at least 40 weight percent of the balm;
   50,000 to 750,000 iu of vitamin A for every 100 ml of carrier solution;
   1,200 to 18,000 iu of vitamin E for every 100 ml of carrier solution;
   250 mg to 3,000 mg of a benzoquinone having a structure of $Q_{10}$; and
   1,000 to 12,000 iu of vitamin D for every 100 ml of carrier solution.

2. The balm of claim 1 additionally comprising up to 2,000 mg of Gamma Linoleic Acid for every 100 ml of said carrier solution.

3. The balm of claim 2 additionally comprising to 9,600 iu of Lecithin for every 100 ml of said carrier solution.

4. The balm of claim 3 wherein the carrier solution is squalene.

5. The balm of claim 4 wherein the percent by weight of each ingredient is about:
   63 percent Squalane;
   8 percent Vitamin A;
   5 percent Vitamin D;
   16 percent Vitamin E;
   1 percent $CoQ_{10}$;
   3 percent Gama Linolein Acid; and
   4 percent Lecithin.

6. The balm of claim 1 further comprising at least one additional ingredient from the following group in the following amounts per 100 ml of carrier solution: a maximum of 2,000 mg of gamma linolenic acid; and a maximum of 16,000 mg of cis linoleic acid.

7. The balm of claim 6 wherein the mixture includes ascorbyl palmitate.

* * * * *

UNITED STATES PATENT AND TRADEMARK OFFICE
CERTIFICATE OF CORRECTION

PATENT NO. : 5,378,461
DATED      : January 3, 1995
INVENTOR(S): Stanley J. Neigut It is certified that error appears in the above-identified patent and that said Letters Patent is hereby corrected as shown below:

Col. 16, Line 23  -  after "comprising" insert --up--

Signed and Sealed this

Seventh Day of March, 1995

Attest:

*Attesting Officer*

BRUCE LEHMAN

*Commissioner of Patents and Trademarks*